United States Patent
Inaba et al.

(10) Patent No.: US 9,462,823 B2
(45) Date of Patent: Oct. 11, 2016

(54) POWDERED PLANT STEROL ESTER-CONTAINING PREPARATIONS, METHOD FOR PREPARING THE SAME AND FOODS AND DRINKS CONTAINING THE SAME

(75) Inventors: Kyoko Inaba, Kawanishi (JP); Hiroshi Oga, Itami (JP); Hozumi Tsubomoto, Takarazuka (JP)

(73) Assignee: MATSUTANI CHEMICAL INDUSTRY CO., LTD., Hyogo (JP)

(*) Notice: Subject to any disclaimer, the term of this patent is extended or adjusted under 35 U.S.C. 154(b) by 856 days.

(21) Appl. No.: 12/000,250

(22) Filed: Dec. 11, 2007

(65) Prior Publication Data
US 2008/0138488 A1    Jun. 12, 2008

(30) Foreign Application Priority Data
Dec. 11, 2006   (JP) .................................. 2006-333344

(51) Int. Cl.
| | |
|---|---|
| A23L 1/30 | (2006.01) |
| A61K 47/00 | (2006.01) |
| A61K 38/17 | (2006.01) |
| A23L 1/308 | (2006.01) |
| A23L 2/52 | (2006.01) |

(52) U.S. Cl.
CPC ............ *A23L 1/3004* (2013.01); *A23L 1/308* (2013.01); *A23L 1/3081* (2013.01); *A23L 2/52* (2013.01); *A23V 2002/00* (2013.01)

(58) Field of Classification Search
CPC ................. A23V 2002/00; A23V 2200/222; A23V 2250/2136; A23V 2200/3262; A23V 2200/326

USPC .................................. 426/601–611, 590, 591
See application file for complete search history.

(56) References Cited

U.S. PATENT DOCUMENTS

| | | | | |
|---|---|---|---|---|
| 4,588,717 A | * | 5/1986 | Mitchell ...................... 514/170 |
| 5,472,732 A | * | 12/1995 | Ohkuma et al. .............. 426/658 |
| 5,620,873 A | | 4/1997 | Ohkuma et al. |
| 6,087,353 A | * | 7/2000 | Stewart et al. ............... 514/182 |

(Continued)

FOREIGN PATENT DOCUMENTS

| | | |
|---|---|---|
| JP | 2-145169 A | 6/1990 |
| JP | 2-154664 A | 6/1990 |

(Continued)

OTHER PUBLICATIONS

Toppan Printing, Emulsified powder and its production, (JP 11196785) Jul. 1999, Manual Translation.*

(Continued)

*Primary Examiner* — Jill Warden
*Assistant Examiner* — Subbalakshmi Prakash
(74) *Attorney, Agent, or Firm* — Sughrue Mion, PLLC

(57) ABSTRACT

This invention provides a preparation of a powdered plant sterol ester which comprises a plant sterol ester, an octenyl succinate-modified starch and an indigestible dextrin. The preparation can be prepared by a method comprising the steps of emulsifying a plant sterol ester in an aqueous solution containing an octenyl succinate-modified starch and an indigestible dextrin to form an emulsion and then powdering the resulting emulsion. The invention permits the application of plant sterol esters to wide variety of foods and drinks. In addition, the invention permits the effective control of an increase of the serum-cholesterol content accompanied by the intake of meals.

8 Claims, 1 Drawing Sheet

(56) References Cited

U.S. PATENT DOCUMENTS

| | | |
|---|---|---|
| 6,623,780 B1 | 9/2003 | Stevens et al. |
| 2002/0064548 A1 | 5/2002 | Yoon et al. |
| 2003/0045473 A1* | 3/2003 | Sarama et al. ............... 514/12 |
| 2004/0013708 A1* | 1/2004 | Goulson et al. ............ 424/439 |
| 2004/0029844 A1 | 2/2004 | Yoon et al. |
| 2004/0131657 A1* | 7/2004 | Wester et al. .............. 424/439 |
| 2004/0247658 A1* | 12/2004 | Trubiano et al. ........... 424/450 |
| 2005/0074536 A1 | 4/2005 | Isomura et al. |
| 2005/0123667 A1* | 6/2005 | Sakuma et al. ............. 426/601 |
| 2006/0035871 A1* | 2/2006 | Auweter et al. ............ 514/169 |

FOREIGN PATENT DOCUMENTS

| | | |
|---|---|---|
| JP | 2662930 B2 | 2/1995 |
| JP | 11-193229 A | 7/1999 |
| JP | 11-196785 A | 7/1999 |
| JP | 11196785 A * | 7/1999 |
| JP | 2003-049189 A | 2/2003 |
| JP | 2003-049190 A | 2/2003 |
| JP | 2003-047359 A1 | 6/2003 |
| JP | 2003-250479 A | 9/2003 |
| JP | 2004-075541 A | 3/2004 |
| JP | 3535147 B2 | 4/2004 |
| JP | 2004-519254 A | 7/2004 |
| JP | 2005-521397 A | 7/2005 |
| JP | 2005-529109 A | 9/2005 |
| JP | 2005-269941 A | 10/2005 |
| WO | WO 0217892 A2 * | 3/2002 |
| WO | 03-086468 A1 | 10/2003 |

OTHER PUBLICATIONS

MatsutaniAmerica.com, Fibersol® -2 in Foods and Beverages, accessed May 8, 2009; http://www.matsutaniamerica.com/fs2/applications.php and Fibersol® -2 Scientific Papers, accessed May 8, 2009; http://www.matsutaniamerica.com/fs2/bib_opsev.php.*

Myriam Richelle, et al., "Both free and esterified plant sterols reduce cholesterol absorption and the bioavailability of β-carotene and α-tocopherol in normocholesterolemic humans 1, 2", the American Journal of Clinic Nutrition, 2004, pp. 171-177, vol. 80.

* cited by examiner

POWDERED PLANT STEROL ESTER-CONTAINING PREPARATIONS, METHOD FOR PREPARING THE SAME AND FOODS AND DRINKS CONTAINING THE SAME

TECHNICAL FIELD

The present invention relates to a powdered plant sterol ester-containing preparation which has improved dispersibility in water, taste, nonhygroscopicity and bioavailability; a method for the production of the preparation; and a food or drink containing the same.

BACKGROUND ART

Plant sterols are substances found in a wide variety of plants such as edible plants including soybeans and rapeseeds and lumbers and they are also called phytosterols. Formal or technical names of these substances are, for instance, β-sitosterol, campesterol, brassicasterol and stigmasterol.

Plant stanols are also called phytostanols and formal or technical names of these substances are, for instance, β-sitostanol, campestanol, brassicastanol and stigmastanol.

In this specification, these phytosterols and phytostanols are generically referred to as "plant sterols" for convenience.

On the other hand, ester derivatives of plant sterols and plant stanols primarily have different formal or technical names depending on substances as counterparts for forming corresponding esters (such as fatty acids) and they are in general referred to as plant sterol esters (phytosterol esters) or plant stanol esters (phytostanol esters). Accordingly, in this specification, these phytosterol esters and phytostanol esters are generically referred to as "plant sterol esters" for convenience.

Sterol corresponds to Sterin in German language and plant sterol esters are also referred to as stearyl esters which are also included in plant sterol esters herein defined.

Plant sterol and cholesterol resemble in their structures and therefore, it has been known that it undergoes competitive inhibition when cholesterol dissolves into bile acid micelles to thus control the absorption of cholesterol in the intestines. As a result, plant sterol permits the reduction of the levels of the overall or total serum cholesterol and of the serum LDL-cholesterol. Accordingly, it has been known that plant sterol is effective for the prevention of diseases such as hyperlipemia, coronary disorders and heart diseases, the US Food and Drug Administration (FDA) has approved that any health-emphasis indication may be attached to a plant sterol ester (or phytosterol)-reinforced food, while the Japanese Ministry of Health and Welfare/Labor has likewise approved some foods to which a plant sterol (or a phytosterol ester) is incorporated, as Foods for Specified Health Use.

It has been reported that plant sterol is rather excellent in bioavailability (ability of a substance to be biologically utilized) as compared with plant sterol ester (Patent Document 1). Regarding bioavailability, however, it has also been reported that both of plant sterol and plant sterol ester show effects of reducing the serum-cholesterol level and effects of inhibiting the absorption of β-carotene, which are comparable level with each other (Non-Patent Document 1). Consequently, there is not any disadvantage in the application of plant sterol ester.

However, plant sterol, which is quite useful as has been discussed above, has such physical properties that it does not dissolve in water and that it may dissolve even in oil in a concentration of only about 1%. Accordingly, plant sterol has been considered to be a material whose application to foods is quite difficult. Under such circumstances, a plant sterol ester has been developed, which shows an excellent solubility in an oil phase, but the kinds of foods, into which the plant sterol ester can be incorporated, are limited to specific ones such as margarine, edible oils, and mayonnaise. This would be quite inconvenient because of such a contradiction that the ingestion of such a plant sterol leads to the simultaneous intake of a large quantity of edible oil. For this reason, it would be an urgent necessity to develop a plant sterol which can easily be dispersed or dissolved even in water. To solve such a problem, there have been done various investigations.

However, most of conventional techniques thus developed relate to methods which comprise the step of emulsifying the plant sterol with the use of a lipophilic emulsifying agent (such as sucrose esters of fatty acids, mono(poly) glycerin esters of fatty acids, polysorbate and lecithin) (Patent Documents 1 to 4) and the resulting preparations are inferior in the taste and texture. In addition, when the emulsion is converted into powder, the resulting powdery preparation is not always considered to be sufficient in its dispersibility in water and the stability in the resulting aqueous solution or dispersion.

Moreover, there have also been proposed various methods which make use of hydrophilic octenyl succinate-modified starch which has good taste (Patent Documents 5 to 7). The resulting products have considerably improved taste, but the powdery preparation derived from the resulting emulsion through conversion thereof into powder still suffers from a problem in dispersibility observed when dissolving the powder in water.

Furthermore, there has been developed a method which comprises the step of emulsifying plant sterol with the use of a sucrose ester of a fatty acid or a polyglycerin fatty acid ester while melting the sterol at a quite high temperature corresponding to its melting point ranging from 120 to 160° C. (Patent Document 1). In the practical preparation thereof, however, the use of a device for controlling the temperature higher than 100° C. would be accompanied by a variety of difficulties from the viewpoint of facilities and energy cost. In addition, the powdered preparation produced according to this method may be applied to any practical food product only with considerable difficulties since the powdered preparation shows very poor dispersibility in water and the re-solubilization thereof in water in turn requires the use of a high pressure homogenizer.

Plant sterol ester is in the form of a paste. Accordingly, when converting the emulsified liquid thereof into powder using dextrin (a basic material for powdering), the hygroscopicity of the resulting preparation is largely dependent upon the magnitude of the hygroscopicity of the dextrin used. Maltodextrin having a DE value ranging from 10 to 25 has a rather weak sweetness and a low hygroscopicity and therefore, it is widely and favorably used as a basic material for powdering, but dextrin having a high DE value ("powdered corn syrup" having a DE value of not less than 25) is naturally superior to the former in view of the dispersibility in water. In this connection, however, the dextrin having a high DE value (powdered corn syrup) conversely has a strong sweetness and a high hygroscopicity and therefore, when applying the same to a food, it may impart undesirable sweetness thereto and the storage stability of the food is adversely affected because of the hygroscopicity thereof. This would become a serious drawback when it is intended to apply the resulting plant sterol to wide variety of foods.

It has been reported that saccharides having a DE value ranging from 10 to 25 are suitably used from the viewpoint of hygroscopicity and water dispersibility thereof when powdering an emulsion of fats and oils (see Patent Documents 10 and 11), but dextrin whose DE value exceeds 10 has a strong sweetness and a high hygroscopicity as has been discussed above and accordingly, it is not necessarily considered as a good basic material for powdering. For instance, PINEDEX #3 having a DE value of 25 (available from Matsutani Chemical Industry Co., Ltd.) shows a good flowability as a powdery substance and is excellent in dispersibility in water, but the product may impart undesirable sweetness to a food containing the same incorporated therein.

It has been reported that a branched dextrin is favorable to improve the dispersibility in water of a spray-dried product derived from an emulsion of a plant sterol (see Patent Document 3), but the branched dextrin is in general dextrin containing branched moieties obtained by removing glucose and low molecular weight oligosaccharides from a product prepared by acting a liquefying amylase on starch and accordingly, the branched dextrin is completely free of any form of linkage other than $\alpha 1 \to 4$ and $\alpha 1 \to 6$ glucoside bonds, which are essential to the starch. Similarly, a highly branched cyclic dextrin is one whose ring structure is formed through hydrolysis and rearrangement of amylopectin clusters by acting a branch-forming enzyme on the linear chain amylose portions connecting amylopectin clusters (see Patent Documents 12 and 13) and accordingly, the cyclic dextrin is also completely free of any form of linkage other than $\alpha 1 \to 4$ and $\alpha 1 \to 6$ glucoside bonds, which are essential for naturally occurring starch. For this reason, these branched dextrins are digestible (hydrolyzable) with a digestive enzyme of the human origin. In addition, no reference has been made with respect to bioavailability of the product obtained through the use of these branched dextrins when powdering the plant sterol.

On the other hand, as dextrins having branched structures different from those observed for the foregoing branched ones, there have been known indigestible dextrins (see Patent Documents 8 and 9). This indigestible dextrin is composed of indigestible water-soluble dietary fibers and therefore, it has been incorporated into wide variety of foods and drinks. Furthermore, it has also been known that the indigestible dextrin can be used as a binder in the preparation of a granulated product (see Patent Document 15), but it has never been used in powdering plant sterol.

Patent Document 6 states that dietary fibers may be added to a plant sterol-containing composition inasmuch as the addition thereof does not adversely affect the intended effect of the composition and polydextrose is specifically described as an example of the water-soluble dietary fiber material. However, polydextrose is a chemically synthesized product and is considered to be a food additive in the United States. In addition, it has been pointed out that polydextrose is liable to cause diarrhea upon ingestion thereof in excess. Further, the Patent Document does not refer to any effect, for instance, dispersibility and bioavailability, observed when it is added to the plant sterol-containing composition.

Moreover, some articles state that a food containing a combination of a plant sterol with dietary fibers (in particular, β-glucan) shows a synergistic effect of reducing cholesterol content (see Patent Document 14). When applying them to foods, however, an important problem has still remained unsolved. For instance, some physical and/or chemical properties such as dispersibility in water and viscosity should further be improved.

Patent Document 1: JP-T-2003-047359;
Patent Document 2: Japanese Patent No. 3,535,147;
Patent Document 3: JP-A-2005-269941;
Patent Document 4: JP-T-2005-521397;
Patent Document 5: Japanese Patent No. 2,662,930;
Patent Document 6: JP-A-2004-75541;
Patent Document 7: JP-T-2005-529109;
Patent Document 8: JP-A-02-145169;
Patent Document 9: JP-A-02-154664;
Patent Document 10: JP-A-11-196785;
Patent Document 11: JP-A-11-193229;
Patent Document 12: JP-A-2003-049189;
Patent Document 13: JP-A-2003-049190;
Patent Document 14: JP-T-2004-519254;
Patent Document 15: JP-A-2003-250479; and
Non-Patent Document 1: Am. J. Clin. Nutr., 2004, 80:171-177.

DISCLOSURE OF THE INVENTION

Problems that the Invention is to Solve

Accordingly, it is an object of the present invention to provide a preparation of a powdered plant sterol ester, which is excellent in dispersibility in water, taste-imparting properties, nonhygroscopicity and bioavailability; a method for preparing such a preparation; and a food or drink containing the same.

Means for Solving the Problems

The inventors of this invention have conducted various investigations to develop such a preparation comprising a powdered plant sterol ester, which is excellent in dispersibility in water, taste-imparting properties, nonhygroscopicity and bioavailability, have found that the foregoing problems associated with the conventional techniques can efficiently be solved by emulsifying and then powdering the plant sterol using octenyl succinate as an emulsifying agent and an indigestible dextrin as a binding material (binder) and have thus completed the present invention.

Accordingly, the present invention herein provides a preparation of a powdered plant sterol ester; a method for producing such a preparation; and a food or drink containing the same, as will be detailed below:
1. A preparation of a powdered plant sterol ester comprising a plant sterol ester, an octenyl succinate-modified starch and an indigestible dextrin.
2. A method for preparing a preparation of a powdered plant sterol ester comprising the steps of emulsifying a plant sterol ester in an aqueous solution containing an octenyl succinate-modified starch and an indigestible dextrin to form an emulsion and then powdering the emulsion.
3. A food or drink which comprises the preparation of a powdered plant sterol ester as set forth in the foregoing item 1.
4. The food or drink as set forth in the foregoing item 3, wherein the food or drink is a drink.

Effects of the Invention

The present invention can herein provide a preparation of a powdered plant sterol ester, which is excellent in dispersibility in water, taste-imparting properties, nonhygroscopicity and bioavailability and a method for preparing such a preparation. Therefore, the present invention permits the application of plant sterol esters to wide variety of foods and drinks. In addition, the present invention in turn permits the effective control of any increase of serum-cholesterol content accompanied by intake of meals, if one takes a meal together with the preparation of the present invention.

BRIEF DESCRIPTION OF THE DRAWINGS

The present invention will now be described more in detail with reference to the following detailed explanation of illustrative embodiments and the accompanying drawings.

BEST MODE FOR CARRYING OUT THE INVENTION

Figure 1:
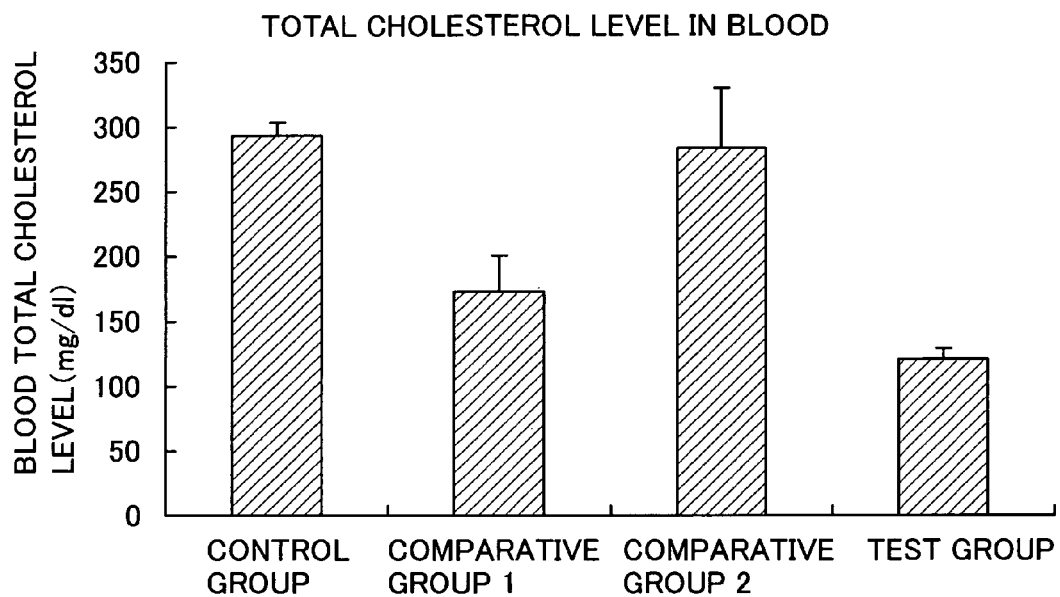
FIG. 1 is a graph showing the results of the total cholesterol content (level) in the blood collected from the animals belonging to the control group, the comparative group 1, the comparative group 2 and the test group (Reference Example 1).

As has already been discussed above, plant sterols include β-sitosterol, campesterol, brassicasterol, stigmasterol, α-sitostanol, campestanol, brassicastanol and stigmastanol and all of the ester compounds of these plant sterols can be used in the present invention. The ester-constituting moieties of the plant sterol esters include, for instance, fatty acids included in edible fats and oils such as oleic acid, linoleic acid, linolenic acid, palmitic acid and stearic acid, but the present invention is not restricted to any particular one.

Examples of methods for the preparation of indigestible dextrin usable in the present invention include a method in which α-amylase is acted on roasted starch (see Patent Document 8); a method in which α-amylase and glucoamylase are acted on roasted starch in this order and then subjecting the resulting product to chromatographic fractionation to thus obtain a dextrin product containing indigestible dextrin-fraction in a high content; a method in which transglucosidase is acted on enzyme-treated roasted starch prior to chromatographic fractionation thereof (see Patent Document 9). These methods comprise, for instance, thermal decomposition steps and enzymatic reactions and therefore, the resulting products are glucans having such highly branched structures each containing α1→2 and α1→3 glucoside bonds in addition to α1→4 and α1→6 glucoside bonds, which are essential to naturally occurring starch and the average molecular weight thereof is about 2,000. By way of example, the indigestible dextrin can commercially be available from, for instance, Matsutani Chemical Industry Co., Ltd. under the trade name of FIBER-SOL 2.

The octenyl succinate-modified starch used in the present invention is starch ester obtained by ester bond formation between a portion of hydroxyl groups of the starch and hydrophobic octenyl succinic acid and it also includes the octenyl succinate-modified starch-hydrolysate obtained by hydrolyzing starch moieties of the starch ester using, for instance, an enzyme.

The starting starch materials may preferably be, for instance, those each having a high amylopectin content such as waxy corn starch, waxy potato starch, glutinous rice starch, but the present invention is not restricted to these specific examples at all.

Any octenyl succinate-modified starch listed above may be used in the present invention without any restriction. However, the starting material for the octenyl succinate-modified starch is a starch and therefore, the modified starch should be dissolved with heating and the resulting product has a high viscosity in a high concentration. For this reason, it may suffer from some problems when using the same in drinks (in particular, powdered beverages) without any pretreatment. Accordingly, to make the modified starch usable in the entire applications, it would be more preferred to use products prepared by hydrolyzing starch moieties of the octenyl succinate-modified starch with an enzyme or an acid; or to use products obtained through physical breakage of the octenyl succinate-modified starch.

In this connection, the hydrolyzation of the octenyl succinate-modified starch is preferably carried out to such an extent that a viscosity of a 20% by mass aqueous solution thereof determined by a Brookfield type viscometer falls within the range of from 20 to 50 mPa·s, but the degree of hydrolyzation is not restricted to any specific range in the present invention.

The octenyl succinate-modified starch used herein may be prepared according to a variety of known methods such as one disclosed in Example II of U.S. Pat. No. 2,661,349. More specifically, to 150 parts by mass (hereunder simply referred to as "part") of water, there is dissolved 2 parts of sodium carbonate, then 100 parts of waxy corn starch and 0.1 part of octenyl succinic acid anhydride are introduced into the resulting sodium carbonate solution with stirring, followed by the reaction of these components for 12 hours, the subsequent control of the pH value to about 7.0, filtration, washing and then drying the reaction product or octenyl succinate-modified starch.

Further, the octenyl succinate-modified starch having favorable forms for use in applications as drinks can be prepared according to, for instance, the method as disclosed in Example I of JP-A-2002-191299. More specifically, a 28% slurry of the octenyl succinate-modified starch is jet steam-cooked at a temperature of 149° C. and then α-amylase and then β-amylase are acted on the steam-cooked starch while controlling the temperature to a level ranging from 85 to 88° C. and the pH values to the optimum levels for the respective enzymes. To the reaction solution, there is directly added steam to deactivate the enzymes followed by spray-drying the reaction product to thus give powdery hydrolysate of the octenyl succinate-modified starch.

The mixing ratio (by mass) of the octenyl succinate-modified starch to the plant sterol ester in the preparation of a powdered plant sterol ester preferably ranges from 1:0.1 to 1:10, more preferably 1:0.5 to 1:5 and further preferably 1:1 to 1:4. This is because if the rate of the octenyl succinate-modified starch is less than 1:10, the resulting emulsion is insufficient in the stability, while if it exceeds 1:0.1, the viscosity of the resulting preparation is too high to easily handle the same and the desired effect of the product as the plant sterol ester preparation would considerably be reduced.

The mixing ratio (by mass) of the indigestible dextrin to the plant sterol ester in the preparation of a powdered plant sterol ester preferably ranges from 1:10 to 1:0.1, more preferably 1:5 to 1:0.2 and further preferably 1:1 to 1:0.5. This is because if the rate of the indigestible dextrin is less than 1:10, the resulting preparation hardly shows considerable improvement of the intended effects such as reduction of the cholesterol content and the water-dispersibility, while if it exceeds 1:01, the water-solubility of the resulting preparation is conversely impaired and further the desired effect of the product as the plant sterol ester preparation would considerably be reduced.

Thus, the powdered plant sterol ester preparation of the present invention can be prepared by blending and emulsifying the plant sterol ester, the octenyl succinate-modified starch and the indigestible dextrin so that the foregoing mixing ratios are satisfied and then powdering the resulting emulsion. In this connection, the presence of the indigestible dextrin is not essential to the powdering of the emulsion, but the addition thereof to the emulsion would show the efficacy as will be further detailed later. Alternatively, it is also possible to prepare a granular preparation by blending the plant sterol ester and the octenyl succinate-modified starch, emulsifying and powdering the resulting mixture and then adding the indigestible dextrin to the powdered product and the resulting granular preparation is also encompassed by the present invention.

The method for preparing such an emulsion is not restricted to any specific one and the emulsion can be prepared according to any conventionally known method. Although the method which makes use of a high pressure homogenizer permits the preparation of such an emulsion in the shortest period of time, but such a high pressure homogenizer is not always used and an emulsion can easily be prepared by treating the ingredients for 10 to 120 minutes and preferably 30 to 60 minutes in an ordinary pressure homogenizer, while the ingredients are blended in such a manner that the foregoing mixing ratios are satisfied. This is quite convenient from the viewpoint of the investment in plant and equipment.

As means for powdering the resulting emulsion, usable herein include, for instance, drum-drying, freeze-drying, and spray-drying and the product of the present invention can be prepared by any one of the foregoing methods without any trouble. In this respect, however, it is desirable in the present invention to select spray-drying in view of saving of energy cost.

When the emulsion is spray-dried, the indigestible dextrin present therein would serve as a basic material for powdering. In other words, the indigestible dextrin can play three rolls at the same time, i.e., it would make the powdering of the emulsion easy, improve dispersibility of the resulting powder in water, and enhance cholesterol-reducing effect of the plant sterol ester. The resulting powder has a low hygroscopicity and it is, therefore, excellent in storage stability and thus it can directly be delivered to consumers. Moreover, the resulting powder has an excellent dispersibility and is less sweet. Accordingly, each consumer may add the powder to his favorite drink or juice and it can be ingested together with a meal and this would be quite convenient for the consumers.

Dispersibility of the resulting preparation can be evaluated, for instance, by visually observing the condition of the preparation when 2.5 g of the same is dispersed in 20 g of water; and taste-imparting properties thereof can likewise be evaluated through sensory test carried out using 4 volunteer panelists; hygroscopicity thereof can be evaluated by allowing the preparation to stand in an open system at room temperature and then visually observing the preparation. In addition, bioavailability thereof is evaluated according to a test in which a high cholesterol and high sucrose-loaded feed is fed to SD-type rats.

The preparation of a powdered plant sterol ester according to the present invention can be ingested alone or in the form of a food or a drink which comprises the preparation as an ingredient thereof. In particular, the preparation of the present invention can easily be applied to all kinds of foods and drinks including, for instance, aqueous foods such as beverages (milk beverages, coffee beverages, nutrient-reinforced drinks, sport drinks, soybean milk beverages or the like), desserts (yogurt, jelly, sherbet or the like), seasonings (dressings, sauces, Tare, miso or the like), soups (curry, stew, potage or the like), and powdery foods (powdered beverages, powdered soups, auxiliary health beverages or the like), and further consumers can ingest the preparation after the direct incorporation thereof into their favorite foods.

It is sufficient to intake the preparation of the present invention in an amount ranging from 0.2 to 2.0 g when it is ingested alone. On the other hand, when the preparation is incorporated into a food or drink, the former is added to the latter in an amount ranging from 0.1 to 1.0% by mass as expressed in terms of the amount of the plant sterol ester, while taking into consideration the kind and characteristic properties of each particular food or drink.

EXAMPLES

The present invention will hereunder be described in more specifically with reference to the following Reference Examples and Examples, but the present invention is by no means limited to these specific Examples.

Reference Example 1

Method for the Preparation of Octenyl Succinate-Modified Starch Hydrolysates

A pH value and temperature of a 30% by mass slurry of waxy corn starch were adjusted to 8.0 and 30° C., respectively, followed by the addition of octenyl succinic acid in an amount of 3.0% by mass based on the total mass of the starch and the subsequent reaction of these components for 3 hours with stirring. The reaction system thus obtained was neutralized, washed and then dried. A pH value of the resulting 35% by mass slurry was controlled to 6.0, KLEISTASE L1 (available from Amano Enzyme Inc.) was added to the slurry in an amount of 0.1% by mass based on the total mass of the starch and the enzyme reaction was continued at 85° C. for about one hour. At this stage, a viscosity of the resulting starch paste (diluted to Brix 20) was determined using a Brookfield viscometer and it was found to be 30 mPa·s. A pH value of the starch paste was adjusted to 3.8, the enzyme was deactivated through heating the paste at 90° C. for 10 minutes, a pH thereof was again controlled to 5.5, the starch paste was filtered through a layer of diatomaceous earth and then subjected to spray-drying to thus give an octenyl succinate-modified starch hydrolysate.

Reference Example 2

Each of basic materials for powdering having the compositions specified in Table 1 was variously evaluated in order to convert, into powder, an emulsion of a plant sterol ester emulsified with an octenyl succinate-modified starch and as a result, it was found that the preparation which made use of indigestible dextrin (formulation 3) was excellent in all of the items examined, i.e., water-dispersibility, taste and nonhygroscopicity.

In this connection, the plant sterol ester used herein was CARDIOAID S (available from ADM Company) and the product prepared in Reference Example 1 was used as octenyl succinate-modified starch, respectively. Moreover, PINEDEX #3 (DE25) and PINEDEX #1 (DE9) are dextrin products manufactured by Matsutani Chemical Industry Co., Ltd. And further FIBERSOL 2 (DE10) is an indigestible dextrin product likewise manufactured and sold by the same company.

TABLE 1

|  | Formulation (part by mass) | | |
| --- | --- | --- | --- |
| Raw Materials | 1 | 2 | 3 |
| Plant sterol ester | 30.0 | 30.0 | 30.0 |
| Octenyl Succinate-Modified Starch | 30.0 | 30.0 | 30.0 |
| PINEDEX #3 (DE25) | 30.0 | — | — |
| PINEDEX #1 (DE9) | — | 30.0 | — |
| Fibersol 2 (DE10) | — | — | 30.0 |
| Water (q.s.: as much as suffice) | q.s. | q.s. | q.s. |
| Results of Evaluation | | | |
| Dispersibility | ◎ | X | ◎ |
| Taste | Δ | ◎ | ◎ |
| Nonhygroscopicity | Δ | ◎ | ◎ |

Evaluation criteria: ◎: quite excellent; ○: excellent; Δ: slightly inferior; X: not acceptable.

Reference Example 3

Feeds each comprising the product of the present invention were inspected for serum-cholesterol content-reducing effect according to the following method:
Animals used: 4-week-old SD type male rats (5 animals per group);
Raising: The animals were kept under the following conditions: temperature: room temperature (22±2° C.); humidity: 60±10%; illumination: during the term extending from 7:00 to 19:00; while they could freely take the feed specified below and drinking water (pure water) over 4 weeks prior to the test;
Compositions of feeds used: See Table 2 given below:

TABLE 2

|  | Formulation (part by mass) | | | |
| --- | --- | --- | --- | --- |
|  | Cont. | Comp. Group 1*) | Comp. Group 2 | Test group**) |
| α-Corn starch | 10.8 | 9.0 | 4.9 | 4.0 |
| Casein | 20.0 | 20.0 | 20.0 | 20.0 |
| Sucrose | 62.0 | 62.0 | 62.0 | 62.0 |
| Corn oil | 0.7 | 0.7 | 0.7 | 0.7 |
| AIN-93 Mineral mixture | 3.5 | 3.5 | 3.5 | 3.5 |
| AIN-93 Vitamin mixture | 1.0 | 1.0 | 1.0 | 1.0 |
| DL-Methionine | 0.3 | 0.3 | 0.3 | 0.3 |
| Heavy choline succinate | 0.2 | 0.2 | 0.2 | 0.2 |
| Cholesterol | 1.0 | 1.0 | 1.0 | 1.0 |
| Sodium salt of cholic acid | 0.5 | 0.5 | 0.5 | 0.5 |
| Plant sterol ester | — | 0.897 | — | 0.897 |
| Octenyl succinate-modified starch | — | 0.897 | — | 0.897 |
| Indigestible dextrin | — | — | 5.0 | 5.0 |
| Citric acid | — | 0.006 | — | 0.006 |
| Total | 100.0 | 100.0 | 100.0 | 100.0 |

*)An emulsified and powdered product of a plant sterol ester, an octenyl succinate-modified starch and citric acid was used.
**)An emulsified and powdered product (Formulation 5) of a plant sterol ester, an octenyl succinate-modified starch, an indigestible dextrin and citric acid was used.

Measurement: Each of the rats raised over 4 weeks using the feeds specified in Table 2 was subjected to the laparotomy under etherized condition, blood was collected through the abdominal aorta, the blood was then centrifuged to give a supernatant (serum) and then the serum was inspected for total cholesterol content, HDL-cholesterol level, and triglyceride level using "Cholesterol E-Test WAKO", "HDL Cholesterol E-Test WAKO" and "Triglyceride E-Test WAKO" (all of them are available from Wako Pure Chemical Industries, Ltd.), respectively, provided that the LDL-cholesterol level was calculated according to the following equation:

$$\text{LDL-Cholesterol} = \text{Total Cholesterol} - (\text{HDL-Cholesterol} + \tfrac{1}{5}\,\text{Triglyceride})$$

Figure 2:
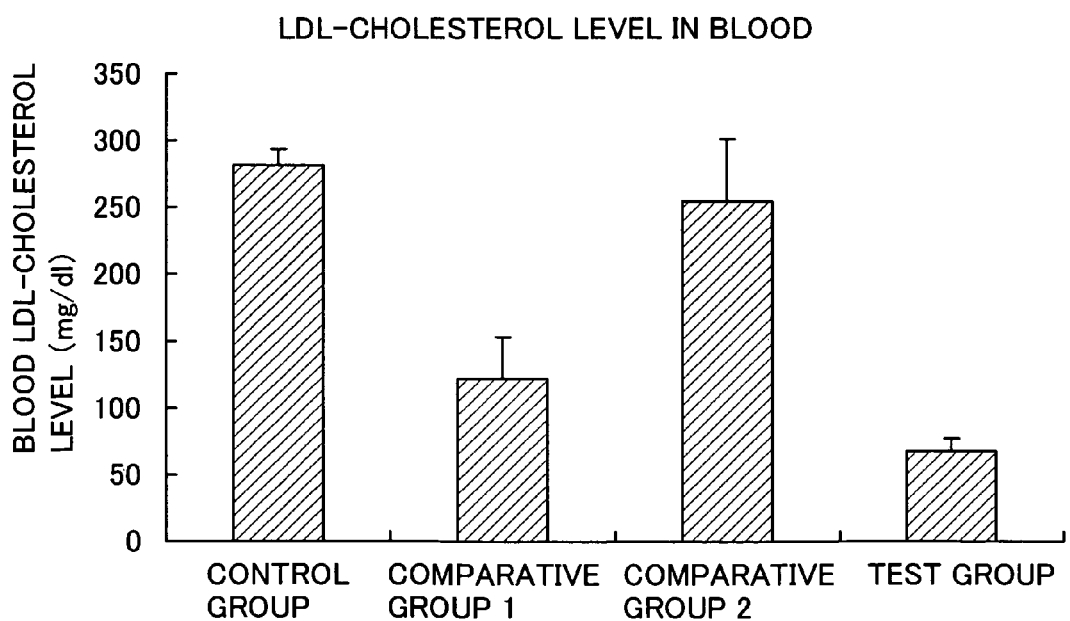
FIG. 2 is a graph showing the results of the LDL-cholesterol content (level) in the blood collected from the animals belonging to the control group, the comparative group 1, the comparative group 2 and the test group (Reference Example 1).

The total cholesterol content (level) and the LDL-cholesterol level in the blood collected from the animal raised over 4 weeks are plotted in FIG. 1 and FIG. 2, respectively. These results clearly indicate that the total cholesterol content (level) and LDL-cholesterol (bad cholesterol) level in the blood were reduced in highest degrees, in the test group in which the test animals took the feed comprising the preparation of the powdered plant sterol ester. This accordingly demonstrated the excellent effect of the simultaneous use of the indigestible dextrin as a basic material for powdering.

In this respect, it was also found that the HDL-cholesterol level in the test group was not reduced and it was conversely increased, although the results were not shown in the foregoing figures.

Example 1

In this Example, there were prepared preparations of powdered plant sterol esters according to the present invention, each having the composition as specified in Table 3:

TABLE 3

| Raw Materials | Formulation 4 (part by mass) | Formulation 5 (part by mass) |
| --- | --- | --- |
| Plant sterol ester | 33.30 | 13.20 |
| Octenyl succinate-modified starch | 33.30 | 13.20 |
| Citric acid | 0.10 | 0.10 |
| Indigestible dextrin | 33.30 | 73.50 |
| Total | 100.00 | 100.00 |
| Water (q.s.: as much as suffice) | q.s. | q.s. |

The mixture having the foregoing formulation 4 or 5 was emulsified in a T.K. homogenizer for 60 minutes and then the resulting emulsion was powdered through spray-drying. Both of these preparations thus formed were found to have acceptable characteristic properties such as fluidity in their powdery states, water-dispersibility and storage stability (each preparation was dispersed in water such that the concentration thereof was equal to 0.2% and 0.6% as expressed in terms of the amount of the plant sterol, the resulting dispersions were allowed to stand at room temperature over 30 days and then they were visually inspected for the presence of, for instance, suspended matters and precipitates).

Example 2

Preparation of Lemon Water (Sports Drink-Like Beverage)

Lemon water was prepared according to the formulation specified in Table 4. As a result, it was found that the product was found to be excellent in dispersibility and taste and it was also found that the preparation was free of any rough feeling to the tongue. Moreover, the lemon water prepared according to the formulation specified in Table 4 was packaged in a 100 ml volume bottle for accommodating drinks, the bottle was heated up to 95° C. in a hot water bath or it was sterilized at a temperature of 85° C. for 30 minutes, followed by cooling with running water and then storing at room temperature over 3 months. As a result, it was found that there was not observed the formation of any suspended matters and precipitates, due to the addition of the preparation of the present invention.

TABLE 4

| Raw Materials | Formulation 6 (part by mass) | Formulation 7 (part by mass) |
|---|---|---|
| Fructose | 5.000 | 5.000 |
| Citric acid | 0.100 | 0.100 |
| Flavor derived from lemon | 0.100 | 0.100 |
| Sodium citrate | 0.050 | 0.050 |
| Vitamin C | 0.020 | 0.020 |
| Potassium chloride | 0.005 | 0.005 |
| Preparation of the invention (Formulation 4) | 1.000 | 3.000 |
| Water | 93.725 | 91.725 |
| Total | 100.000 | 100.000 |

Example 3

Preparation of Coffee-Milk Drink

Coffee-milk drink was prepared according to the formulation specified in Table 5. As a result, it was found that the product was found to be excellent in dispersibility and taste and it was also found that the preparation was free of any rough feeling to the tongue. Moreover, the coffee-milk drink prepared according to the formulation specified in Table 4 was heated up to 60° C. and then emulsified in a T.K. homogenizer (5,000 rpm, 5 minutes) and a high pressure homogenizer (200 kg/cm$^2$, one pass). Each of the resulting products was packed in a 100 ml volume heat-resistant bottle, then retort-sterilized at 125° C. for 20 minutes, followed by cooling with running water and then storing at room temperature for 3 months. As a result, it was found that there was not observed the formation of any suspended matters and precipitates, due to the addition of the preparation of the present invention.

TABLE 5

| Raw Materials | Formulation 8 (part by mass) | Formulation 9 (part by mass) |
|---|---|---|
| Extract from coffee beans | 54.000 | 54.000 |
| Milk | 9.500 | 9.500 |
| Granulated sugar | 5.500 | 5.500 |
| Sugar ester | 0.030 | 0.030 |
| Sodium hydrogen carbonate | 0.120 | 0.120 |
| Preparation of the invention (Formulation 5) | 2.520 | 7.560 |
| Water | 28.330 | 23.290 |
| Total | 100.000 | 100.000 |

What is claimed is:

1. A preparation of a powdered plant sterol ester consisting of a plant sterol ester, an octenyl succinate-modified starch and an indigestible dextrin, or a preparation of a powdered plant sterol ester consisting of a plant sterol ester, an octenyl succinate-modified starch, an indigestible dextrin and citric acid, wherein the indigestible dextrin is a glucan having a highly branched structure and containing α1→2 and α1→6 glucoside bonds and α1→4 and α1→6 glucoside bonds, and wherein the content of the indigestible dextrin is within a range from 33.3 to 73.5% by mass based on the total amount of the preparation.

2. A method for preparing a preparation of a powdered plant sterol ester consisting of a plant sterol ester, an octenyl succinate-modified starch and an indigestible dextrin and optionally citric acid comprising the steps of emulsifying a plant sterol ester in an aqueous solution containing an octenyl succinate-modified starch and an indigestible dextrin and optionally citric acid to form an emulsion and then powdering the emulsion, wherein the indigestible dextrin is a glucan having a highly branched structure and containing α1→2 and α1→3 glucoside bonds and α1→4 and α1→6 glucoside bonds, and wherein the content of the indigestible dextrin is within a range from 33.3 to 73.5% by mass based on the total amount of the preparation.

3. A food or drink which comprises the preparation of a powdered plant sterol ester as set forth in claim 1.

4. The food or drink as set forth in claim 3, wherein the food or drink is a drink.

5. The preparation of a powdered plant sterol ester as set forth in claim 1 which has nonhygroscopicity.

6. The preparation of a powdered plant sterol ester as set forth in claim 1, wherein the octenyl succinate-modified starch and the plant sterol ester are present in a mixing ratio by mass of the octenyl succinate-modified starch to the plant sterol ester in the preparation of a powdered plant sterol ester of from 1:1 to 1:4.

7. The method for preparing a preparation of a powdered plant sterol ester as set forth in claim 2, wherein the preparation shows nonhygroscopicity.

8. The method for preparing a preparation of a powdered plant sterol ester as set forth in claim 2, wherein the octenyl succinate-modified starch and the plant sterol ester are in a mixing ratio by mass of the octenyl succinate-modified starch to the plant sterol ester in the preparation of a powdered plant sterol ester of from 1:1 to 1:4.

* * * * *